US008840935B2

(12) United States Patent
Haber et al.

(10) Patent No.: US 8,840,935 B2
(45) Date of Patent: Sep. 23, 2014

(54) ORALLY ADMINISTRABLE FILMS AND PREPARATION THEREOF

(75) Inventors: Meir Haber, Netanya (IL); Thordis Kristmundsdottir, Seltjarnarnes (IS); Skuli Skulason, Kapvaogur (IS)

(73) Assignee: Biota Ltd., Netanya (IL)

( * ) Notice: Subject to any disclaimer, the term of this patent is extended or adjusted under 35 U.S.C. 154(b) by 842 days.

(21) Appl. No.: 12/226,879

(22) PCT Filed: Apr. 30, 2007

(86) PCT No.: PCT/IL2007/000525
§ 371 (c)(1),
(2), (4) Date: Feb. 17, 2009

(87) PCT Pub. No.: WO2007/125533
PCT Pub. Date: Nov. 8, 2007

(65) Prior Publication Data
US 2009/0186107 A1 Jul. 23, 2009

(30) Foreign Application Priority Data
May 1, 2006 (IL) .......................................... 175338

(51) Int. Cl.
*A61K 36/00* (2006.01)
*A61K 36/534* (2006.01)
*A61K 9/00* (2006.01)
(52) U.S. Cl.
CPC ..................................... *A61K 9/006* (2013.01)
USPC ............ 424/725; 424/747; 424/434; 424/435
(58) Field of Classification Search
None
See application file for complete search history.

(56) References Cited

U.S. PATENT DOCUMENTS

| 4,140,760 | A | 2/1979 | Withington |
| 6,596,298 | B2 * | 7/2003 | Leung et al. ................... 424/435 |
| 6,709,671 | B2 | 3/2004 | Zerbe et al. |
| 2004/0043134 | A1 | 3/2004 | Corriveau et al. |
| 2004/0115137 | A1 | 6/2004 | Verrall et al. |
| 2004/0156794 | A1 | 8/2004 | Barkalow et al. |
| 2004/0208931 | A1 | 10/2004 | Friend et al. |
| 2004/0247648 | A1 | 12/2004 | Fadden et al. |
| 2004/0247649 | A1 | 12/2004 | Pearce et al. |
| 2005/0031675 | A1 | 2/2005 | Spence Leung et al. |
| 2005/0036977 | A1 | 2/2005 | Gole et al. |

FOREIGN PATENT DOCUMENTS

| WO | 2005/048980 | 6/2005 |
| WO | 2007/073346 | 6/2007 |

OTHER PUBLICATIONS

Davis, "Drug Delivery Systems", Interdisciplinary Science Reviews, 2000, vol. 25, No. 3, pp. 175-183.
Eouani et al., In-vitro comparative study of buccal mucoadhesive performance of different polymeric films, European Journal of Pharmaceutics and Biopharmaceutics, vol. 52, 2001, pp. 45-55.
Haber et al., "Polymeric Films for Oral Administration of Bioactive substances," 4th Eastern Mediterranean Chemical Engineer Conference, Israel, 2006, pp. 336-339.
Hermes et al., "Polymeric Alginate Films and Alginate Beads for the Controlled Delivery of Macromolecules," Trends Biomater. Artif. Organs., vol. 15(2), pp. 54-56, 2002.
Jasti et al., "Recent Advances in Mucoadhesive Drug Delivery Systems," Business Briefing: Pharmatech, 2003, pp. 194-196.
Peh, "Polymeric Films as Vehicle for Buccal Delivery: Swelling, Mechanical, and Bioadhesive Properties," J. Pharm. Pharmaceut. Sci., 1999, 2(2), pp. 53-61.
Puttipipatkhachorn et al., "Drug physical state and drug-polymer interaction on drug release from chitosan matrix films," Journal of Controlled Release, vol. 75, 2001, pp. 143-153.
Rhim, "Physical and mechanical properties of water resistant sodium alginate films," Lebensmittel-Wissenschaft und-Technologie, 2004, vol. 37(3), pp. 323-330.
Shojaei, "Buccal Mucosa As a Route for Systemic Drug Delivery: A Review," J. Pharm. Pharmaceut. Sci. 1(1), pp. 15-30, 1998.
"Alginates for Pharmaceutical Applications", ISP Alginates, Code: PHARMA/ALG/0901, 2001, 6 pages.
Klanke, "Dissolution Testing of Orally Disintegrating Tablets," Dissolution Technologies, May 2003, pp. 6-8.
International Search Report for PCT/IL2007/000525, mailed Dec. 19, 2007.
S. Al-Musa et al., "Evaluation of Parameters Involved in Preparation and Release of Drug Loaded in Crosslinked Matrices of Alginate", Journal of Controlled Release, Elsevier Science Publishers B.V., Amsterdam, NL, vol. 57, No. 3, Feb. 22, 1999, pp. 223-232, XP004159025.
C. Remunan-Lopez et al. "Mechanical, Water Uptake and Permeability Properties of Crosslinked Chitosan Glutamate and Alginate Films", Feb. 17, 1997, Journal of Controlled Release, Elsevier, Amsterdam, NL, pp. 215-225, XP000636961.
P. Aslani et al., "Studies on Diffusion in Alginate Gels. I. Effect of Cross-Linking with Calcium or Zinc Ions on Diffusion of Acetaminophen", Journal of Controlled Release, Elsevier, Amsterdam, NL, vol. 42, No. 1, Oct. 1, 1996, pp. 75-82, XP000620285.
Kulkarni et al. "Exploration of Different Polymers for use in the Formulation of Oral Fast Dissolving Strips", Journal of Current Pharmaceutical Research, 2010; 2(1); 33-35.
"Alginic Acid, Sodium Salt", www.mobio.com/ecom/docs/proddata.nsf/(webtds2)/218295, Jul. 12, 2011.
"Alginates for Pharmaceutical Applications", Code: PHARM/ALG/0901, ISP Alginates, 2001, 6 pages.
Murata, et al., "Preparation of Fast Dissolving Films for Oral Dosage from Natural Polysaccharides," Materials, 2010, 3, 4291-4299; doi: 10.3390/ms3084291.

* cited by examiner

*Primary Examiner* — Chris R Tate
*Assistant Examiner* — Randall Winston
(74) *Attorney, Agent, or Firm* — Graeser Associates International Inc; Dvorah Graeser

(57) ABSTRACT

The invention relates to an orally administrable mucoadhesive film which comprises one or more bioactive ingredients and, as a major film-forming polymer, at least one alginate which is capable of forming a low viscosity aqueous solution. Also provided is a process for preparing such films.

21 Claims, No Drawings

ORALLY ADMINISTRABLE FILMS AND PREPARATION THEREOF

This application is the U.S. national phase of International Application No. PCT/IL2007/000525 filed 30 Apr. 2007 which designated the U.S. and claims priority to IL 175338 filed 1 May 2006, the entire contents of each of which are hereby incorporated by reference.

Oral administration of bioactive substances (BAS) in the form of tablets or capsules is extensively applied in the pharmaceutical and nutritional supplements industry. However, using films for administration of BAS has several advantages over conventional forms.

Application of films as fast dissolving (FD) dosage form eliminates the need of swallowing, use of water for administration, and hazard of chocking. Thus FD films enable delivery of BAS via the digestive tract overcoming the difficulty with swallowing (Dysphagia) of conventional forms, a dysfunction of about 35% of the general population, mainly common at children and elderly population.

The flexibility and large area of films are especially advantageous for mucosal delivery systems (MDS), since these features contribute to delivery properties, comfort and ease of use (Davis, 2000). MDS are applied in order to accomplish first-pass administration (without passing the digestive tract) of BAS to or via mucosal membranes, and as compared to other MDS forms (e.g., sprays, gels) films are clean, simple, concentrated, exact dose (Shojaei, 1998).

Films are matrix system, where BAS are dispersed in polymer, where release of BAS is due to the diffusion of BAS out of the matrix and/or due to the disintegration of the matrix.

Polymers are widely used in the pharmaceutical industry as coating agents in tablet formulations. Polymers are used to protect the tablet core from the surroundings, improve appearance, mask bad taste, and control release from the tablet. However the use of polymeric films, especially as MDS has not been widely adopted.

Although the preparation technique and the polymers incorporated in MDS and FD films may be similar, there are distinct differences between the properties of these two delivery systems as detailed below.

The ideal FD or MDS film should be flexible, but strong enough to endure the physical stress of administration and friction in the mouth. Swelling of the film if present should not be too excessive to avoid discomfort and should not cause increase in area of the film (Peh and Wong, 1999).

Principally, FD and MDS films are composed of a polymer film-forming carrier incorporated with a BAS and additives intended to improve the films' handling properties, taste, and BAS stability or absorption. However, FD films dissolve completely within a very short period of time (usually few seconds), but MDS films require good mucoadhesive properties and long residence time (at least few minutes) in order to direct the BAS flux towards the mucosal membrane and bloodstream.

Both FD and MDS films should dissolve or disintegrate without leaving substantial residue that can be felt by the human tongue or which needs to be swallowed or ejected from the mouth. However, in order to secure long residence time and directional flow of BAS, non-disintegrating, single or multi-laird MDS films may be applicable. The drawback of such films is that swallowing of the film should preferably be avoided. Furthermore, removal of the film from application site after application may cause discomfort or damage the mucosal membrane. FD forms may have several terminologies describing the same form as detailed in, e.g., U.S. Patent Application 2005/0036977. U.S. Patent applications 2004/208931, 2004/247649, 2005/0031675, and U.S. Pat. No. 6,709,671 (2004) describe few FD film compositions with benefits or advantages ascertained to polymeric or other ingredients as compared to other formulations.

Primary application of currently available commercial FD strips is for breath freshening. The breath-fresheners market leaders are Cool Mint Listerine PocketPaks® distributed in the US by Warner Lambert (Pfizer) and Eclipse®, distributed by Wrigleys. Several additional breath-fresheners are distributed in the US and Europe under various brand names and privet labels. The success of breath-freshener strips led to commercialization of additional FD strips such as vitamin or herbal remedies, and caffeine, as well as dissolving and non-dissolving strips for tooth whitening.

The major distinction between FD forms and swallowed forms is the need to mask the usually bitter or otherwise adverse taste of most of the drugs so taste masking by encapsulation of the drug or addition of sweeteners or taste masking flavors is usually required in FD formulation (Klancke, J., 2003).

Furthermore, MDS may require incorporation of penetration enhancers and additional additives in order to enable permeation of the BAS trough the mucosal membrane, and to stabilize the BAS during permeation and bloodstream circulation.

The main difference between MDS and FD films is residence time. FD films should dissolve or disintegrate in a mouth within very short period of time (usually few seconds) and be transferred by the saliva for absorption of the BAS in the gastro-intestinal tract. MDS films should have long residence time (from few minutes to few hours) and release the BAS so it will be absorbed by or via the mucosal membrane of the oral (or other mucosal) cavity.

FD forms may be very useful administration system of APIs to children or for CNS and geriatric disease treatment. Children and patients of CNS diseases, e.g., Multiple Sclerosis, Alzheimer's or Parkinson's disease, and especially very young children and CNS patients with advanced disease, have difficulties or even have no physical or mental capacity to swallow pills. Therefore an orally dissolving delivery system could make a substantial increase in the compliance of such populations, thus improve their quality of life. However, several FD tablets require the patient to move the tablet in the mouth by the tongue or chew it in order to achieve disintegration, which is also difficult or impossible for these populations.

MDS are attractive for BAS delivery because mucosal membranes are thin and permeable. MDS may be applicable for delivery of various BAS, including biopharmaceuticals such as peptides, proteins, vaccines, etc.

Several mucoadhesive delivery systems have been developed including mucoadhesive tablets, gels, ointments, patches and films. Mucoadhesive films are better choice than tablets in terms of softness and comfort. Films are not easily rinsed away be saliva as gels, and films can also cover ulcers and thus physically reduce the pain endured by patients (Peh, K. K., Wong C. F., 1999). Being administered to a mucosal surface, the film absorbs fluids, swells, partially or entirely disintegrates and releases the active agent.

The rate at which the BAS is released from the film is determined by a number of factors. These factors include: the chemistry and concentration of the BAS, chemistry and concentration of polymers and other inactive ingredients, and the dimensions of the film, mainly film thickness. The thickness of the film is a factor in determining the rate of the film disintegration and an active agent release: increasing the thickness of the film increases the disintegration time. Generally, a thick film will disintegrate slower than a thin film. A thick film, however, may be desirable for its higher loading capacity for BAS that are administered in high dosages. Increased thickness has effect on the rate of the BAS flow from the film that is faster in a thinner film because of the destruction of the matrix (Justi, B., et. al., 2003, Putipipatkhachorn, S. et. al., 2001).

Further to film forming the film is usually cut into strips, each strip usually contains a single dosage unit. The size of the strip may be varied according to the dosage required. The BAS dosage contained in each strip is predetermined by formulation. In order to differentiate the product, or for promotional or advertising purposes, it is possible to cut the film, or printing onto it, a logo or otherwise reputable shape or figure.

Ideal FD and MDS films should respond to a large number of requirements:
1. They should possess fast disintegration or reasonably good bioadhesive strength to the oral mucosa.
2. They should release the BAS in desired rate and direction.
3. Swelling before disintegration should not be too extensive to prevent discomfort.
4. They should not require water for administration yet dissolve or disintegrate in the oral cavity.
5. They should have pleasing or at least acceptable organoleptic (mouth feel) properties.
6. They should allow sufficient drug loading.
7. They should leave minimal or no residue in the mouth after oral administration.
8. They should not induce damage or peel the epithelium of the mucosal membrane.
9. They should be compatible with taste masking.
10. They should be portable without shelf-life concerns.
11. They should be manufactured using conventional film processing and packaging equipment at low costs.
12. They should be flexible, elastic, and soft yet adequately strong to withstand the manufacturing process and administration.
13. They should exhibit low sensitivity to environmental conditions such as humidity and temperature.

Films properties are controlled by composition of polymers and additives applied for the film forming (Peh K. K., Wong C. F., 1999; Eouani, C., et. al., 2002; Jasti, B., et. al., 2003). The main ingredients for forming a film in solvent-evaporation technique are: polymeric film-forming agent, BAS, and solvent that most of it is evaporated during the film forming process. Additional ingredients are incorporated in order to modulate the film's properties including, mucoadhesion, saliva stimulation, softening-plasticizing, stabilizing, emulsifying, taste masking, thickening, binding, coloring, surfactants, fillers, preservatives, buffering agents, permeation enhancers, sweeteners, flavors and fragrances, and the like.

The polymers used for forming MDS or FD films are hydrophilic and/or water-dispersible and more preferably water-soluble. Film-forming polymer may be either synthetic or natural. Examples of natural polymers are hyluaronic acid and its derivative, starch and modified starch, alginates, chitosan, chitin, natural gums, proteins such as gelatins, collagen, casein, zein, gluten, soy protein isolate, whey protein isolate, and land plant extracts such as pectin, and combinations thereof. Examples of water-soluble synthetic polymers are cross linked polyacrylic acid chains, polyvinyl pyrrolidone, polyvinyl alcohol, modified cellulose ethers such as hydroxypropylmethyl cellulose, hydroxyethyl cellulose, hydroxypropyl cellulose, carboxymethyl cellulose, and ion-exchange resin. The effective amount of the film forming agent ranges from approximately about 10% to about 90%, more preferably 25% to about 75% dry weight depending of the film composition. Examples of FD formulations utilizing various polymers are described in, e.g., U.S. Pat. No. 6,709,671 (2004), and U.S. Patent Applications No. 20040247649, 20040247648, 20050036977.

Numerous polymers have been applied for forming MDS films. When the polymer hydrates, it connects with the mucus and can withstand saliva clearance, tongue movement and swallowing for a certain period of time. On the other hand hydrophilic polymers can swell too much forming a slippery gel and thus loose adhesive properties (Remunán-Lopez, C., Bodmeier, R., 1997). Several processes have been proposed for manufacturing of films. Hot-melt extrusion, solid dispersion extrusion, molding, rolling, spraying, semi-solid casting, and solvent casting may be applied for the film production. Water-soluble polymers including hydrocolloids are mainly applicable for solvent casting while thermoplastic materials such as starch are mainly applicable for extrusion.

Film forming by solvent casting employs a polymer that is completely dissolved or dispersed in the solvent under mixing to form a homogeneous consistency, for example, polyvinyl alcohol-polyethylene glycol graft co-polymer in a 1:1 ethanol-water mixture, described in U.S. Patent Application No. 20040208931. Obtained mixture is degassed and coated onto a smooth surface, for example, polyester film, and dried under aeration, for example, at a higher temperature. A drying phase may be designed as air-drying, baking, vacuum drying or dehydrating by circulating warm air. Dry film is rolled up at a rolling station for later cutting to desired dimensions, packaging and storage. Dry film formed by this process is a glossy stand alone, self-supporting, non-tacky and flexible film.

In certain methods of the film preparation, the film-forming ingredients are mixed and hydrated with water separately from the water-soluble ingredients, which are mixed in aqueous solution separately from the organic ingredients and surfactants. In these methods, the final formulation may be produced by mixing the film-forming phase with the aqueous phase, then mixing in the organic phase, which includes surfactants, such as Polysorbate 80 and Atmos 300. This mass is mixed until emulsified as described in U.S. Patent Application No. 20040247649. In other techniques, the aqueous and film forming phases are combined into a single phase by dissolving the water-soluble ingredients in the water. The organic phase is then added to this single aqueous phase. The resulting formulation is cast on a suitable substrate and dried to form a film.

Further to cutting into strips, the unusable residues are sometime re-hydrated and used again to make new film, thus improving cost efficiency.

Alginic acid and its water soluble alginates are natural polysaccharide polymers extracted from algae that have been used by the pharmaceutical and other industries for many years and for numerous applications in various forms such as films for tablet coating, fibers for wound care, and gels for drug delivery (Anon. 2001).

Alginates are high molecular weight polysaccharides extracted with dilute alkali from various species of brown seaweeds (kelp). They are hydrophilic colloidal carbohydrates that are water-soluble biopolymers of colloidal nature when hydrated. In terms of chemical structure, they are linear copolymers of 1,4 linked β-D mannuronic acid and β-L-guluronic acid that consist of three distinct polymer segments: Polymannuronic acid segments (M blocks), polyguluronic acid segments (G blocks), and alternating mannuronic acid and guluronic acid units (MG blocks) A wide range of these polymers are offered as alginic acid, various salt forms, and propylene glycol esters that vary in molecular weight, particle size, M/G ratio, and viscosity. Alginate is of interest as a potential biopolymer film or coating component because of its unique colloidal properties, which include thickening, stabilizing, suspending, film forming, gel producing, and emulsion stabilizing. Alginic acid and its derivatives have been used in food processing industry, in biotechnology industry for producing beads for immobilization of cells or enzymes in pharmaceutical industry for tablet disintegration, controlled release, encapsulation, as films and coatings, lubricating agents, prevention of gastric reflux, gelling and as thickening agents to stabilize emulsions and suspensions (Anon., 2001).

Sodium alginate is a natural, biocompatible, biodegradable and hydrophilic polymer suitable for the entrapment of bioactive ingredients, for example, drugs. Sodium alginate hydrates readily in water, the solutions are stable in the pH range of 4-10 and upon drying form strong transparent films.

Properties of MDS films using various polymeric compositions including sodium alginate have been recently described (Haber M., et. al. 2006).

Use of one or more ionic cross-linkers to modify alginate Film's hydrolytic properties is well known, e.g., two different methods of $CaCl_2$ treatment, i.e. the direct addition of $CaCl_2$ into film-making solution and the immersion of alginate films into $CaCl_2$ solutions have been proposed (Rhim, J-W., 2004). However, it was shown that crosslinked alginate in a matrix form has limitation in practical use for drug delivery due to the effect of acidic medium on the crosslinking of the matrix film and hence, the rate of drug release (Al-Musa S, et. al., 1999) and slow release of large molecules from crosslinked alginate film (Hermes, R. S., Narayani, R., 2002).

It has now been found that it is possible to prepare alginate-based films satisfying a combination of desirable properties for orally administrable films.

In one aspect, the present invention provides an orally administrable mucoadhesive film which comprises a bioactive ingredient and, as a major film-forming polymer, an alginate; wherein said alginate is capable of forming a low viscosity aqueous solution.

The term "alginate", as used herein, collectively refers to alginic acid, salts and esters thereof, and most preferably, to sodium alginate. By the term "major" is meant that the concentration of the alginate in the film provided by the present invention is greater than any other film-forming polymer that may be optionally included in said film. Preferably, the film comprises not less than 30%, more preferably not less than 40%, even more preferably not less than 50% and most preferably not less than 75% alginate, expressed in terms of weight percent relative to the total weight of the film.

An alginate that may be suitably used according to the present invention is capable of forming a low viscosity aqueous solution at room temperature at a concentration of 1% (w/v). More specifically, the alginate for use according to the invention is an alginate, which upon dissolution in water in a concentration of 1% (w/v), at a temperature of 20° C., forms an aqueous solution having a viscosity value of less than 1000 cP. According to one embodiment of the invention, the viscosity measured for 1% (w/v) aqueous solution of the alginate is in the range between 500 and 1000 cP. According to an alternative embodiment, the alginate selected for preparing the film is such that the viscosity of 1% (w/v) aqueous solution thereof is less than 100 cP, and preferably in the range between 10 to 70 cP at a temperature of 20° C. The viscosity measurements may be carried out on a Brookfield viscometer, spindle N° 2, at 20 rpm to 60 rpm.

Additional viscosity tests that may be used for identifying preferred alginates to be practiced according to the present invention may be carried out at different concentrations of the alginate and/or different temperatures.

For example, a preferred alginate is this, which upon dissolution in water at a concentration of 5% (w/v) at temperature of 20° C., forms an aqueous solution having a viscosity value of less than 8000 cP.

Suitable alginates meeting the aforementioned requirements are commercially available and few such alginates are mentioned in the Examples below.

The term "BAS", as used herein, encompasses pharmaceutically or biologically active substances such as drugs, pharmaceuticals, nutrition supplements, medications, vitamins, homeopathic remedies, herbal remedies and the like, or mixtures thereof.

Active pharmaceutical ingredients (APIs) which may be formulated into the alginate based films provided the present invention include both large and small, either water soluble or insoluble molecules, intended for treatment of various diseases or health disorders, including antibacterial, antiviral and anti-inflammation agents, and APIs that affect the CNS function for treatment of migraine, Multiple Sclerosis, Parkinson's or Alzheimer's diseases, depression, dementia, anxiety, insomnia, fatigue, etc.

Examples of pharmaceutically active compounds that may be formulated into the films of the present invention may be selected from the group consisting of the following compounds: triptans, donepezil, memantine, resageline, selagiline, zaleplon, olanzepine, fluoxantine, buspirone, maxalate, phenylhydantoin, phenobarbital, primidone, carbamazepine, ethosuximide, methsuximide, phensuximide, trimethadione, diazepam, benzodiazepines, phenacemide, pheneturide, acetazolamide, sulthiame bromide, gabapentin and phenytoin.

Herbal remedies, which may be formulated into the films provided the present invention, include, inter alia, licorice, ginseng and menthol.

Nutritional supplements, which may be formulated into the films provided by the present invention include, inter alia, water or lipid soluble vitamins, minerals, antioxidants, and the like. Non-limiting examples include: vitamin A, B, lycopene, β-carotene, lutein, selenium, and the like.

The amount of the BAS in the formulation may be adjusted to deliver a predetermined dose of the BAS. Generally, the amount of the BAS in the dry film is from 0.1% to 80% by weight, preferably from 1% to 25% by weight based on the total weight of the dried film. Particularly preferred APIs are selected from the group consisting of risperidone and pharmaceutically acceptable salts thereof, tamsulosin and pharmaceutically acceptable salts thereof, escitalopram and pharmaceutically acceptable salts thereof, memantine and pharmaceutically acceptable salts thereof, donepezil and pharmaceutically acceptable salts thereof, triptans and pharmaceutically acceptable salts thereof.

Particularly preferred BAS other then APIs are selected from the group consisting of licorice, mint, lycopene, β-carotene, natural antioxidants, minerals, and vitamins.

The films provided by the present invention contain sodium alginate capable of forming a low viscosity aqueous solution as the major film-forming polymer. However, if desired, additional water-soluble synthetic or natural film forming polymers may be incorporated in the film composition. These include polyvinyl alcohol, pectin, cellulose derivatives such as cellulose gum, hydroxyethyl cellulose, hydroxypropyl cellulose, hydroxypropylmethyl cellulose (HPMC), carboxymethyl cellulose, poly acrylic acid, and the like.

The films provided by the present invention may contain, in addition to alginate and one or more bioactive ingredients, also suitable additives such as softeners, absorption enhancers, binding agents, thickening agents, surfactants, stabilizing agents, cooling agents, natural or artificial sweeteners, food colorants and dyes, and saliva stimulating agents.

To improve flexibility and reduce the brittleness of the films a softener, also known as a plasticizing agent, may be incorporated. Suitable plasticizing agents are polyols (sorbitol, glycerin, polyethylene glycol, propylene glycol, glycerol monoesters with fatty acids or other pharmaceutically acceptable polyalcohols), hydrogenated starch hydrolysates, corn syrups, L-menthol. Glycerin, sorbitol, polysorbate 80, triethyl titrate, acetyl triethyl titrate, and tributyl titrate are considered as especially useful softeners for oral-mucosal contact. The concentration of the plasticizing agent in the dry film can range between 0.1 and 20% (w/w).

Absorption enhancers facilitate the absorption of macromolecules by increasing their diffusion, and, thus, they are very useful for increasing the absorption of drugs or other active agents with poor permeability. There are two ways of passive diffusion of macromolecules through the buccal mucosal membrane: intracellular and intercellular. Intercellular spaces and cytoplasm are hydrophilic; lipophilic substances have low solubility in this environment. Oppositely, cell membrane is rather lipophilic and hydrophilic drugs have limited permeation through the cell membrane. Therefore, intercellular spaces are a major barrier for lipophilic compound permeation. Cell membranes are a major transport barrier for hydrophilic compounds. Since the oral epithelium is stratified, solute permeation may involve a combination of these two routes.

Useful binding agents may be starch, casein and pullulan. Suitable thickening agents may be cellulose ethers, synthetic polymers such as polyvinyl pyrrolidone, polyvinyl alcohol, polyethylene glycol, water-dispersible polyacrylates like polyacrylic acid, etc. To reduce the "slimy" texture of the compositions, bulk filler agents such as magnesium and calcium carbonate, calcium phosphate, calcium sulfate, clay and microcrystalline cellulose may be included.

To reduce the surface tension of water, surfactants may optionally be included in the film. Useful examples of surfactants include mono and diglycerides of fatty acids and polyoxyethylene sorbitol esters. The total concentration of surfactants in the final film may be between 0.1 and 5% w/w depending on the properties of the other ingredients.

Useful stabilizing agents include xanthan gum, locust bean gum and carrageenan, in amounts ranging from about 0 to about 10 wt % or otherwise. Cooling agent such as monomenthyl succinate in amounts ranging from about 0.001 to about 2.0 wt % may optionally be incorporated. To improve manufacturability and consistency of the film containing oil (which normally would not mix with the water component), emulsifying agents (0-5 wt %) are included. Examples are casein, triethanolamine. stearate, quaternary ammonium compounds, acacia, gelatin, lecithin, bentonite, veegum, and the like. Natural and artificial flavoring approved in Chemicals Used in Food Processing, publication 1274 by the National Academy of Sciences, pages 63-258, may be optionally used. Natural and artificial sweeteners such as monosaccharides, aspartame, acesulfame potassium, saccharine, sucralose, soluble saccharin salts, dipeptide based sweeteners, etc. can impart an aftertaste of the films. Natural food colorants and dyes suitable for food and drugs can also be incorporated in the film composition. Saliva stimulating agents such as citric, malic and ascorbic food acids can also be incorporated in amount of 0.01-12 wt %.

In another aspect, the present invention provides a process, which comprises providing at least one alginate which is capable of forming a low viscosity aqueous solution as described hereinabove, preparing a liquid mixture containing at least one bioactive ingredient and said alginate, wherein said alginate is the major film-forming polymer present in said mixture, casting said liquid mixture onto a suitable carrier, drying said liquid mixture to obtain a film and removing said film from said carrier.

The liquid mixture may be prepared in the form of a clear solution, suspension, dispersion or emulsion based on water or aqueous alcohol, according to the physical and chemical properties of the ingredients to be formulated (their solubility, hydrolytic stability, etc.). Preferably, the viscosity of the liquid mixture prepared is not more than 10,000 cP at temperature of 50° C.

Formulation for casting is prepared by adding while stirring sodium alginate powder to water, which is most preferably distilled or deionized water. The concentration of the alginate is preferably not greater then 5% (w/v). Other ingredients to be included in the formulation may be premixed with the alginate powder, or may be separately added to the water. It is advantageous to preheat the water before the introduction of the alginate and/or other ingredients thereto. The preheating provides better dissolution, reduction of viscosity and removal of air from the water that otherwise, may oxidize active or inactive ingredients and may form bubbles during the drying stage. To facilitate the dissolution of the alginate, the alginate-water mixture may be further heated with constant stirring until the alginate and other ingredients are completely dissolved as indicated by formation of a clear solution. The heating may then be stopped or continued depending of the properties of other ingredients of the formulation that are incorporated into the film. The one or more bioactive ingredients may be added to the alginate solution as is (for example, as a powder) or as a separate solution of this ingredient in an appropriate solvent. Said solvent may be distilled or deionized water or water miscible organic solvent (for example, ethanol, acetone, etc) or water-organic solvent mixture in various rates. Other ingredients that may be present in of the formulation, as indicated hereinabove (such as plasticizers, optional additional film forming agents, absorption enhancers, thickening agents, surfactants, stabilizing agents, emulsifying agents, flavoring agents, colorants, saliva stimulating agent and the like) may be introduced to the solution by the same technique.

Prepared formulation may be filtered through appropriate mesh filter, in order to remove foam and possible impurities, and is subsequently transferred onto a carrier provided with a flat surface made of suitable material (e.g., a casting mold or a band conveyer having a polystyrene, polyester, polyurethane, stainless steel, or silicone coated surface). It is preferred to carry out the casting step. such that the casting solution is still hot, the temperature thereof being above 50° C., and possibly above 70° C.

The solution is then dried at ambient or elevated temperature to evaporate the solvent. Depending of the physical and chemical properties of the formulation ingredients (solubility, hydrolytic and thermal stability), the evaporation of the solvent is usually carried out at an elevated temperature or at several distinct temperatures (preferably a first stage of drying at a low temperature and subsequent stages of drying at higher temperatures). In the case of stable components, such drying temperatures allow decreasing drying time to a few minutes. However, the drying process should be performed in such temperatures that do not cause component destruction or modification nor influence the film disintegration rate or other physical qualities of forming bubbles in the film or shell hardening, or otherwise cause operational problems such as uneven drying or lifting off of the film from the substrate.

Having completed the evaporation of the solvent, the resulting dried film, having thickness in the range of 10 to 400 micrometer, and more preferably in the range of 25 to 150 micrometer, may be peeled off from the carrier and laminated onto another suitable substrate (a liner) such as silicon coated paper in order to enable cutting and/or re-use of the casting carrier. The laminated film is de-laminated, cut to desirable shape and size, packaged in single, or multiple unit dose container, and labeled.

The films provided by the present invention are strong and flexible, adhere to oral cavity mucosal membrane, and residence time of such films is adjustable in wide range. Accordingly, the films provided by the present invention may serve either as FD films and, alternatively, as MDS, by appropriately formulating the film. The concentration of the plasticizing agent for the FD and MDS films may vary within a wide range. However, FD films usually require the addition of salivating agents in order to enable rapid disintegration of the film, and MDS usually require the addition of other polymers, and/or crosslinking by means of calcium ions.

More specifically, the present invention provides mucoadhesive FD films having residence time in the range between 30 and 120 seconds, and MDS films having residence time in the range between 10 minutes to few hours.

Upon placement on the tongue of FD film provided by the present invention, it tends to stick to the upper palate of the mouth without the ability to peel it off, and is then disintegrated or dissolved by the saliva, whereby the possibility of said film being removed or ejected from the mouth or swallowed before disintegration thereof is practically impossible.

Administration of the MDS film of the invention is usually by adhering it to any specifically preferred targeted location at an oral cavity mucosal membrane, whereby the removal of the adhered film before disintegration or release of the BAS is practically impossible.

The following non-limiting list of alginates and examples are used to illustrate the invention.

EXAMPLES

The table below lists five alginates available from three manufacturers, which alginates were found to be suitable in forming the films of the invention. The viscosity values refer to 1% (w/v) aqueous solution of the alginate, and were determined by means of Brookfield viscometer (RVT or LV) under the conditions specified below:

| Alginate | Viscosity (cP) |
| --- | --- |
| Manucoal LF, ISP | 10-40 (spindle N°2, 60 rpm) |
| Protanal LF 10/60, FMC | 20-70 (spindle N°2, 60 rpm) |
| Protanal LF 10/60 LS, FMC | 20-70 (spindle N°2, 60 rpm) |
| Satialgine S 1100, Degussa | 550-750 (spindle N°2, 20 rpm) |
| Satialgine S 1600, Degussa | 800-1000 (spindle N°2, 20 rpm) |

The alginates listed above were used for preparing both fast dissolving mucoadhesive films and long residence mucoadhesive films as described below. The residence time and mucoadhesion properties of the films are modulated by the formulation as illustrated in the examples.

FD Films

Example 1

Licorice-containing Film

An amount of 8.4 g sodium alginate (Manucol LF, ISP Alginates), and 2.2 g of sucrose was dissolved in 200 ml of distilled water at 50° C. An amount of 790 mg of licorice paste J (FC Licorice, Israel) containing 12% (w/w dry base) of glycerrhizin and 168 mg of licorice flavor no. 77890-33 (Givaudan, Switzerland) was mixed with 210 ml of the alginate-sucrose solution. The resulting suspension was cast on polyester Petri dishes with total area of 1500 cm$^2$ and dried at ambient temperature for 24 hours under constant airflow in a chemical hood. The dried film obtained had a thickness of 85±10 µm. The dried film was tested for oral disintegration acceptance (taste, adhesion and disintegration rate). The film was found to have licorice taste, to have good adhesion to roof of the mouth, and oral cavity disintegration of less than two minutes.

Example 2

Risperidone-containing Film

An amount of 33 mg. Risperidone was dissolved in 15 ml of boiling ethanol containing 250 mg of sorbitol. Then, 0.50 g of hydroxyethyl cellulose (Natrosol 250G Pharma, Aqualone France) and 5 ml of deionized water were added and the mixture was heated to boiling point. A clear solution was obtained. Separately, an amount of 1.0 g sodium alginate (Manucol LF, ISP Alginates), 0.30 g of glycerol and 50 mg of ascorbic acid was dissolved in 25 ml of hot deionized water at 90° C. Then, these two solutions (ethanolic and aqueous) were mixed together. The resulting solution was cast onto polyester Petri dish having 9 cm in a diameter and dried in a dark at ambient temperature for 24 hours under constant airflow in a chemical hood as it is described above. The dried film having thickness of 85±5 µm was tested for oral disintegration acceptance (taste, adhesion and disintegration rate). The film was found to have slight bitter taste, to have good adhesion to roof of the mouth, and oral cavity disintegration of less then one minute.

Example 3

Tamsulosin-containing Film

An amount of 36.3 mg Tamsulosin hydrochloride was added at 60° C. to 50 ml of aqueous solution containing 1.5 g of sodium alginate (Protanal LF, FMC Biopolymer) and 350 mg of sorbitol. The resulting solution was cast on two 9 cm-diameter polyester Petri dishes and dried at ambient temperature under constant airflow in a chemical hood. The dried film was tested for oral disintegration acceptance (taste, adhesion and disintegration rate). The film was found to have slight bitter taste, to have good adhesion to roof of the mouth, and oral cavity disintegration of less then one minute.

Example 4

Escitalopram-containing Film

The composition of the formulation and the amounts of the ingredients are shown in the table below. Citric acid was dissolved in 200 ml of distilled water and then sodium alginate (Protanal LF10/60, FMC Biopolymer), glycerol and sucrose were added and dissolved at 60° C. The obtained solution was cooled to ambient temperature and, then, Aspartame, Escitalopram Oxalate and Fantasy flavor were added and dissolved therein. The resulting solution was cast onto casting mold having casting area of 1,150 cm² and dried according to Example 3.

| Ingredient | Amount, g |
| --- | --- |
| Escitalopram Oxalate (Titan Pharma, India) | 0.920 |
| Protanal LF10/60 (FMC Biopolymer) | 6.000 |
| Glycerol | 0.4180 |
| Sucrose | 2.400 |
| Aspartame | 0.486 |
| Fantasy 11031-31 (Givaudan, Switzerland) | 0.0915 |
| Citric acid | 0.0853 |
| Water | 200 |

The dried film, 70±6 μm thickness, was tested for oral disintegration acceptance (taste, adhesion and disintegration rate). The film was found to have slight bitter taste, to have good adhesion to the roof of the mouth, and oral cavity disintegration of less then one minute. Additionally, stability of Escitalopram in the film was tested using accelerated shelf life test and it was found to be stable. Disintegration rate of the film was tested using USP apparatus II and it was found that disintegration time was between 40 to 60 seconds.

Example 5

Lycopene-containing Film

An amount of 100 mg agglomerated Lyc-O-Mato® 70% powder (Lycored, Israel) and 505 mg sucrose were grinded using mortar and pastel, and mixed with 1.0 g of Protanal® LF 10/60LS (FMC Biopolymer). The mixture was added slowly to 30 ml of preheated to 90° C. deionized water, and 69 mg glycerol was added. The mixing was continued until a uniform suspension was formed. Obtained suspension was cast on polyester Petri dishes with total area of 100 cm² and dried at ambient temperature for 24 hours under constant airflow, in a dark, in a chemical hood.

The dried film was tested for oral disintegration acceptance (taste, adhesion and disintegration rate). The film was found to have slight tomato taste, to have good adhesion to the roof of the mouth, and oral cavity disintegration of less then one minute. Additionally, stability of lycopene in the film was tested using pure oxygen for ten days as accelerated shelf life test.

It was found that the lycopene content was decreased by 2.5%, indicating the lycopene stability in the film at ambient temperature in dark for at least one year.

Example 6

Memantine-containing Film

The composition of the formulation and the ingredient content are shown in the table below.

| Ingredient | Amount, g |
| --- | --- |
| Protanal ® LF 10/60 LS (FMC Biopolymer) | 1.5 |
| Memantine HCl (Lachema, Czech Republic) | 0.160 |
| Sucrose | 0.623 |
| Glycerol | 0.919 |
| Aspartame | 0.167 |
| Pericol Ato 5 ® (Gattefosse, France) | 0.126 |
| Water | 50 |

Sodium alginate (Protanal LF10/60, FMC Biopolymer), glycerol and sucrose were added to 50 ml of distilled water and dissolved at 60° C. The obtained solution was cooled to ambient temperature and, then, Aspartame, Memantine and Pericol Ato were added and dissolved therein. The resulting solution was cast onto casting mold having casting area of 200 cm² and dried according to Example 3. The dried film was turbid, with no visible crystals. The dried film was tested for oral disintegration acceptance (taste, adhesion and disintegration rate). The film was found to have slightly bitter taste, to have good adhesion to roof of the mouth, and oral cavity disintegration of less then one minute.

Example 7

Film Containing Vitamin B Complex

The composition of the formulation and the ingredient content are shown in the table below.

| Ingredient | Amount, g |
| --- | --- |
| Manucol LF (ISP Alginates) | 4.5 |
| Sucrose | 1.5 |
| Vitamin B1 | 0.015 |
| Vitamin B3 | 0.200 |
| Vitamin B6 | 0.020 |
| Fantasy 11031-31 (Givaudan) | 0.0260 |
| Aspartame | 0.0271 |
| Water | 150 |

Sodium alginate (Manucol LF, ISP Alginates) was dissolved in 150 ml of distilled water, afterwards, other ingredients were added as in was described in Example 4. The obtained solution was cast onto casting mold having casting area of 625 cm² and dried according to Example 3. Dried film was tested for oral disintegration acceptance (taste, adhesion and disintegration rate). The film was found to be tasteless, to have good adhesion to roof of the mouth, and oral cavity disintegration of less then one minute.

Example 8

Donepezil-containing Film

The composition of the formulation and the ingredient content are shown in the table below. The preparation of the casting solution and the drying techniques are as described in Example 4. Casting area was 625 cm².

| Ingredient | Amount, g |
| --- | --- |
| Protanal LF10/60 (FMC Biopolymer) | 3.50 |
| Donepezil (100%) (ChimAgis, Israel) | 1.00 |
| Sucrose | 1.00 |
| Aspartame | 0.0772 |
| Glycerol | 0.100 |
| Citric acid | 0.100 |
| Water | 100 |

The dried film was tested for oral disintegration acceptance (taste, adhesion and disintegration rate). The film was found to have slightly bitter taste, to have good adhesion to roof of the mouth, and oral cavity disintegration of less then one minute.

Long Residence Films

Example 9

Licorice-containing Film

An amount of 6.0 grams of sodium alginate (Manucol LF, ISP Alginates) and 1.0 gram Noveon AAl (Noveon, Inc.) were dissolved in 200 ml of distilled water at 60° C. An amount of 1.6 grams of licorice paste J (FC Licorice, Israel) containing 12% (w/w dry base) of glycerrhizin was mixed with the solution. The resulting suspension was cast on polyester Petri dishes with total area of 625 cm$^2$ and dried at ambient temperature for 36 hours under constant airflow in a chemical hood.

The dried film was subjected to cross-linking treatment by immersion in 50 ml aqueous solution containing 0.155 mg $CaCl_2$ and 0.259 mg citrus pectin (Sigma P-9135) for 100 seconds. Excess solution was discarded, and the film re-dried.

Obtained film had a thickness of 130±10 μm. The film was evaluated for taste, mucoadhesion, and residence time. The film was found to have licorice taste, strong and lasting adhesion to buccal mucosa, and oral cavity residence time of over ten minutes.

Example 10

Sumatriptan-containing Film

The composition of the formulation and the ingredient content are shown in the table below. Propylene glycol and sumatriptan were added to premixed 2% (w/v) distilled water solutions of sodium alginate and HPMC. The resulting solution was cast onto casting mold having casting area of 240 cm$^2$ and dried according to Example 3.

| Ingredient | Amount, g |
| --- | --- |
| 2% Satialgine S 1100 (Degussa, France) | 84 |
| 2% HPMC 4000 (NMD, Norway) | 36 |
| Propylene glycol (NMD, Norway) | 120 |
| Sumatriptan succinate (Dr. Reddy's, India) | 0.7 |

The dried film was found to have good adhesion to oral cavity mucosal membranes.

Sumatriptan release assay and film disintegration time were tested using film area of 3.61 cm$^2$ and HPLC method. Assay was conducted according to the USP/NF XXIII, Drug Release Setup for Transdermal Delivery Systems, with one adjustment of using 37° C. instead of 32° C. temperature of the receiving medium, which was composed of a 0.05 M $KH_2PO_4$ buffer at pH 6.75.

Up to 80% of the incorporated sumatriptan was released within 10 minutes. During the release the film swelled but did not disintegrate until 25-30 minutes, indicating it's in-vivo oral mucosa residence time will be longer then the time required for sumtriptan release, thus enabling the trans-mucosal delivery of sumatriptan.

Example 11

Mint-containing Film

The composition of the formulation and the ingredient content are shown in the table below. Preparation of casting solution and drying techniques were. as those described in Example 4. Casting area was 625 cm$^2$.

| Ingredient | Amount, g |
| --- | --- |
| Manucol LF (ISP Alginates) | 6.0 |
| Citrus pectin (Sigma, USA) | 1.00 |
| Blue color #1 | 0.022 |
| Aqua menthapiparate | 1 |
| $CaCl_2$ | 0.10 |
| Aspartame | 0.137 |
| Water | 200 |

Obtained film had a thickness of 110±2 μm. The film was evaluated for taste, mucoadhesion, and residence time. The film was found to have sweet mint taste, strong and lasting adhesion to buccal mucosa, and oral cavity residence time of about fifteen minutes.

Example 12

Mint-containing Film

The composition of the formulation and the ingredient content are shown in the table below. Propylene glycol and Aqua menthapiparate were added to premixed 2% (w/v) distilled water solutions of sodium alginate and HPMC. The resulting solution was cast onto casting mold having casting area of 240 cm$^2$ and dried according to Example 3.

| Ingredient | Amount, g |
| --- | --- |
| 2% Satialgine S 1600 | 84 |
| 2% HPMC 4000 (NMD, Norway) | 36 |
| Propylene glycol (NMD, Norway) | 120 |
| Aqua menthapiparate | 1 |

The dried film was found to have good adhesion to oral cavity mucosal membranes.

Disintegration time of the film according to the assay described in example 10 was about 40-60 minutes.

REFERENCES

Al-Musa S, et. al.: Evaluation of parameters involved in preparation and release of drug loaded in crosslinked matrices of alginate. *J. Control Release,* 1999, 57 (3): 223-32.

Anon.: Alginates for pharmaceutical applications. ISP Alginates. 2001 Code: PHARMA/ALG/0901.

Davis S. S.: Drug Delivery Systems. *Interdisciplinary Science Reviews,* 25 (3): (2000): 175.

Eouani, C. C. et. al.: In-vitro comparative study of buccal mucoadhesive performance of different polymeric films. *Eur. J. Pharma. Biopharm.* 52 (2002) 45-55.

Haber, M. et. al.: Polymeric films for oral administration of bioactive substances. 4th Eastern Mediterranean Chemical Engineer Conference, Israel. (2006): 336-339.

Hermes, R. S., Narayani, R.: Polymeric Films and Alginate Beads for the Controlled Delivery of Macromolecules, *Trends Biomater. Organs.,* 2002, 15(2): 55-56.

Jasti, B., et. al.: Recent Advances in Mucoadhesive Drug Delivery. *Business Briefings:. Pharmatech* 2003:193-196.

Klancke, J: Dissolution testing of orally disintegrating tablets. *Dissolution technologies, May* 2003.

Peh, K. K., Wong C. F.: Polymeric Films as Vehicle for Buccal Delivery: Swelling, Mechanical, and Bioadhesive Properties. *J. Pharm. Pharmaceut. Sci.*, 1999, 2(2): 53-61.

Putipipatkhachorn, S. et.al.: Drug physical state and drug-polymer interaction on drug release from chitosan matrix films. *J. Cont. Release* 2001, 75: 143-153.

Remunán-Lopez, C., Bodmeier, R. Mechanical, water uptake and permeability properties of crosslinked chitosan glutamate and alginate films, *Journal of Controlled Release* 1997, 44: 215-225.

Rhim, J-W.: Physical and mechanical properties of water resistant sodium alginate films. *Lebensmittel-Wissenschaft und-Technologie*, 2004, 37(3), 323-330.

Shojaei, H. Buccal mucosa as a route for systemic drug delivery: A review. *J. Pharm. Pharmaceut. Sci.*, 1998, 1(1): 15-30.

U.S. Patent Application No. 20050036977
U.S. Patent Application No. 20050031675
U.S. Patent Application No. 20040247648
U.S. Patent Application No. 20040247649
U.S. Patent Application No. 20040208931
U.S. Pat. No. 6,709,671 (2004)

The invention claimed is:

1. An orally administrable mucoadhesive film which comprises at least one bioactive ingredients, and, as a major film-forming polymer, at least one alginate selected from the group of alginates which upon dissolution in water at a concentration of 1% (w/v), at temperatures of 20° C., form an aqueous solution having a viscosity value in the range between 20 and 1000 cp, and which upon dissolution in water at a concentration of 5% (w/v), at a temperature of 20° C., form an aqueous solution having a viscosity value of less than 8000 cP, wherein said film further comprises a plasticizing agent.

2. A film according to claim 1, wherein the concentration of the alginate is not less than 50%, relative to the total weight of the film.

3. A film according to claim 1, wherein the concentration of the alginate is not less than 75%, relative to the total weight of the film.

4. A film according to claim 1, wherein the alginate is selected from the group of alginates which upon dissolution in water at a concentration of 1% (w/v), at temperature of 20° C., form an aqueous solution having a viscosity value of 20 cP to 100 cP.

5. A film according to claim 4, wherein the alginate is selected from the group of alginates which upon dissolution in water at a concentration of 1% (w/v), at temperature of 20° C., form an aqueous solution having a viscosity value in the range between 20 and 70 cp.

6. A film according to claim 1, wherein said film is an orally disintegrable fast dissolving mucoadhesive film which disintegrates in the oral cavity within 30 to 120 seconds.

7. A film according to claim 1, wherein the bioactive ingredient is selected from the group consisting of risperidone and pharmaceutically acceptable salts thereof, tamsulosin and pharmaceutically acceptable salts thereof, escitalopram and pharmaceutically acceptable salts thereof, memantine and pharmaceutically acceptable salts thereof, donepezil and pharmaceutically acceptable salts thereof, triptans and pharmaceutically acceptable salts thereof, natural bioactive materials, licorice, mint, lycopene, beta carotenes, natural antioxidants and vitamins.

8. A film according to claim 1, wherein the alginate is sodium alginate.

9. The film according to claim 1, wherein the bioactive ingredient is water soluble.

10. A film according to claim 1, wherein the bioactive ingredient is lipid-soluble.

11. A film according to claim 1, having thickness in the range of 25 to 150 micrometer.

12. A film according to claim 1, comprising sucrose as a plasticizing agent.

13. An orally administrable mucoadhesive film which comprises at least one bioactive ingredient, wherein the bioactive ingredient is lipid soluble and, as a major film-forming polymer, at least one alginate selected from the group of alginates which upon dissolution in water at a concentration of 1% (w/v), at temperatures of 20° C., form an aqueous solution having a viscosity value in the range between 20 and 1000 cp, and which upon dissolution in water at a concentration of 5% (w/v), at a temperature of 20° C., form an aqueous solution having a viscosity value of less than 8000 cP, wherein said film further comprises a plasticizing agent.

14. An orally administrable mucoadhesive film which comprises at least one bioactive ingredient, wherein the bioactive ingredient is selected from the group consisting of risperidone and pharmaceutically acceptable salts thereof, tamsulosin and pharmaceutically acceptable salts thereof, escitalopram and pharmaceutically acceptable salts thereof, memantine and pharmaceutically acceptable salts thereof, donepezil and pharmaceutically acceptable salts thereof, triptans and pharmaceutically acceptable salts thereof, licorice, mint, lycopene, beta carotenes, natural antioxidants, vitamins, selagiline, zaleplon, olanzepine, fluoxantine, buspirone, maxalate, phenylhydantoin, phenobarbital, primidone, carbamazepine, ethosuximide, methsuximide, phensuximide, trimethadione, diazepam, benzodiazepines, phenacemide, pheneturide, acetazolamide, sulthiame bromide, gabapentin and phenytoin; and, as a major film-forming polymer, at least one alginate selected from the group of alginates which upon dissolution in water at a concentration of 1% (w/v), at temperatures of 20° C., form an aqueous solution having a viscosity value in the range between 20 and 1000 cp, and which upon dissolution in water at a concentration of 5% (w/v), at a temperature of 20° C., form an aqueous solution having a viscosity value of less than 8000 cP, wherein said film further comprises a plasticizing agent.

15. A process for preparing a film containing a bioactive ingredient, which comprises providing at least one alginate selected from the group of alginates which upon dissolution in water at a concentration of 1% (w/v), at temperature of 20° C., form an aqueous solution having a viscosity value in the range between 20 and 1000 cp, and which upon dissolution in water at a concentration of 5% (w/v), at a temperature of 20° C., form an aqueous solution having a viscosity value of less than 8000 cP, preparing a liquid mixture containing at least one bioactive ingredient, a plasticizer and said alginate, wherein said alginate is the major film-forming polymer present in said mixture, casting said liquid mixture onto a suitable carrier, wherein the temperature of the liquid mixture that is transferred onto the carrier is not less than 50° C., drying said liquid mixture to obtain a film and removing said film from said carrier.

16. A process according to claim 15, wherein the viscosity of the liquid mixture prepared is not more than 10,000 cP at temperature of 50° C.

17. A process according to claim 15, wherein the alginate used forms, upon dissolution in water in a concentration of 1% (w/v) at temperature of 20° C., an aqueous solution having a viscosity value of 20 cP to 100 cP.

18. A process according to claim 15, wherein the temperature of the liquid mixture that is transferred onto the carrier is not less than 70° C.

19. A process according to claim 15, wherein the liquid mixture comprises sucrose.

20. The process of claim 15, wherein the bioactive ingredient is water soluble.

21. The process of claim 15, wherein the bioactive ingredient is lipid-soluble.

* * * * *